United States Patent [19]

Arnvidarson et al.

[11] Patent Number: 5,739,034
[45] Date of Patent: Apr. 14, 1998

[54] DETERMINATION OF EXTRANEOUS WATER IN MILK SAMPLES, OR THE FREEZING POINT DEPRESSION OF MILK SAMPLES

[75] Inventors: Börkur Arnvidarson, Nivå ; Lars Nygaard, Græsted; Per Waaben Hansen, Hillerød, all of Denmark

[73] Assignee: Foss Electric A/S, Hillerod, Denmark

[21] Appl. No.: 663,044

[22] PCT Filed: Dec. 9, 1994

[86] PCT No.: PCT/DK94/00462

§ 371 Date: Jun. 10, 1996

§ 102(e) Date: Jun. 10, 1996

[87] PCT Pub. No.: WO95/16201

PCT Pub. Date: Jun. 15, 1995

[30] Foreign Application Priority Data

Dec. 10, 1993 [DK] Denmark ................................ 1385/93

[51] Int. Cl.[6] .................... G01N 33/06; G01N 33/18
[52] U.S. Cl. .................... 436/23; 436/39; 436/150
[58] Field of Search .................... 436/26, 23, 39, 436/150; 424/7.1, 10

[56] References Cited

FOREIGN PATENT DOCUMENTS 0182564  5/1986  European Pat. Off. .
9306460  4/1993  WIPO .
9319364  9/1993  WIPO .

OTHER PUBLICATIONS

Koops et al. (1989). Neth. Milk Dairy J. 43:3–16.
Janatsch et al. (1989). Anal. Chem. 61:2016–2023.
Martens et al. (1989). Norwegian Food Reserarch Institute, Multivariate Calibration, pp. 276–277.

*Primary Examiner*—James Ketter
*Assistant Examiner*—Iran Yucel
*Attorney, Agent, or Firm*—Birch, Stewart, Kolasch & Birch, LLP

[57] ABSTRACT

The present invention relates to a method for quantitatively assessing the amount of any extraneous water contained in a milk sample, the method comprising the steps of (a) performing a determination of the infrared (IR) attenuation of the sample in at least one waveband, (b) quantitatively assessing the amount of any extraneous water in the sample on the basis of the determination (a) and predetermined regression coefficients derived from multivariate calibration with respect to the relationship between infrared attenuation in the at least one waveband and the amount of extraneous water. The invention furthermore relates to a similar method for determining the freezing point depression of the sample. In addition, the invention relates to a method for the establishment of a set of regression coefficients for use in an instrument which determines the amount of extraneous water or the freezing point depression of a milk sample.

50 Claims, 6 Drawing Sheets

DETERMINATION OF EXTRANEOUS WATER IN MILK SAMPLES, OR THE FREEZING POINT DEPRESSION OF MILK SAMPLES

FIELD OF THE INVENTION

The present invention relates to improvements in the determination of extraneous water in milk samples, or in the determination of the freezing point depression of milk samples.

Like the fat content of raw milk, any content of extraneous or added water is a quality parameter of the milk. However, unlike the fat content, the amount added or "extraneous" water in the raw milk may not exceed certain limited values, as higher contents than such values indicate a deficient management of the production or directly fraudulent addition of water to the raw milk. Thus, e.g., national Danish rules prescribe that a warning should be issued when the amount of added or extraneous water in raw milk exceeds 2% by weight, and that an excess of 4% of extraneous water gives rise to a penalty. For these reasons, determination of the amount of any extraneous water is an important determination in the quality control of milk.

DESCRIPTION OF THE RELATED ART

The conventional determination of extraneous water follows a program according to which a freezing point determination is performed at certain prescribed intervals. The freezing point depression of milk (relative to water) is directly related to the osmotic pressure in the milk, which is constant due to the biological processes involved in the cow's production of the milk. Thus, a reduction in the numeric value of the freezing point depression from a normal level indicates the presence of extraneous water, and the numeric size of the reduction is indicative of the amount of extraneous water in the milk. The determination of the freezing point depression is performed by means of a cryoscope in which the milk sample is cooled at a constant rate, and the temperature at which the freezing of the milk initiates is determined. This is a time-consuming process, and thus, there is a demand for a more efficient and fast method of determining the freezing point depression, or directly the amount of extraneous water in a milk sample.

The present invention provides a method in which the amount of extraneous water in a milk sample, or the freezing point depression of a milk sample, can be determined in a fast and efficient manner, using equipment of a type which is already acknowledged routine equipment in the quality control of milk.

"Routine testing of farm tank milk by infra-red analysis . . .", J Koops et al, Neth. Milk Dairy J. 43 (1989), pp 3–16, discloses a method for the determination of the freezing point depression of milk by combining a measurement of the electric conductivity of the sample and a determination ("prediction") of the contents of lactose, fat and protein of the sample using a well-known infra-red analysing system.

In this reference, the determination of the freezing point depression of the sample is based on the concentrations of fat, lactose and protein such as these are determined in accordance with the infra-read analysis methods used. This has a number of limitations: Firstly, any minor component, such as citric acid or urea, is not included in the measurement, which can result in systematic errors because the effect of these minor components on the freezing point depression cannot be taken into consideration. Secondly, any random errors in the determination of the fat, lactose or protein may reappear with increased intensity in the prediction of the freezing point depression.

SUMMARY OF THE INVENTION

According to the present invention, it has been found that the determination of the freezing point depression by means of an infra-red analyzer can be improved by increasing the calibration leverage of the samples by including milk samples to which water has been deliberately added in the samples used for calibration of the infra-red analyzer, compared to the method of the above-mentioned reference according to which the calibration is performed using natural bulk milk samples. Also other methods of increasing the calibration leverage of the samples will improve the determination of the freezing point depression, such as explained in detail in the following. Furthermore, it has been found that it is not necessary to include the concentration of fat, lactose and protein in the determination of the freezing point depression of the sample, but that the determination can advantageously be based on the measurement of infrared attenuation directly without any conversion thereof to any concentration value. This measurement can be performed in a lower number of wavebands than would be used for the determination of the concentration of all of fat, lactose and protein, for example using only wavebands in which lactose predominantly absorbs, but on the other hand, is has been found to be highly advantageous to include also information on the minor components of milk in the infra-red determination, again without a prior conversion of such information to a concentration value of such components. In other words, the result of the infra-red determination is preferably used directly, normally with standardisation against water and an analogue/digital conversion as the only processing of the data resulting from the measurement. These measures according to the invention result in an increased exactitude of the determination of the freezing point depression.

Furthermore, it has been found possible according to the present invention to directly determine the amount of any extraneous water in milk samples, without first determining freezing point depression and converting the freezing point depression to a measure of the amount of extraneous water. This has been made possible by a particular calibration method, in which the calibration is based on the inclusion of milk samples containing known amounts of extraneous water. Thereby, a new and direct standard method for the determination of extraneous water in milk samples is made possible and is expected to replace determinations based on the indirect method via the freezing point depression.

Thus, in one aspect, the invention relates to a method for quantitatively assessing the amount of any extraneous water contained in a milk sample, the method comprising the steps of:

a) performing a determination of the infra-red attenuation of the sample in at least one waveband, b) quantitatively assessing the amount of any extraneous water in the sample on the basis of the determination (a) and pre-determined regression coefficients derived from multivariate calibration with respect to the relationship between infrared attenuation in the at least one waveband and the amount of extraneous water.

In the present specification and claims, the term "extraneous water" designates water which is not natively present in the milk sample as withdrawn from the cow by manual milking. The extraneous water may be water deriving from incomplete draining of the milking equipment after cleaning, or water left in tanks before the milk is filled therein, etc. Of course, the water could also be water deliberately and fraudulently added to increase the volume of the milk delivered.

The determination of the infra-red attenuation is performed in at least one waveband, but normally in a number of wavebands or, using e.g. a Fourier transform interferometer, over a detailed continuous range of wavebands. In accordance with well-known infra-red measuring techniques, the measurements may be performed as dual beam dual cell measurements or single beam single cell measurements, and each measurement in a waveband is normally combined with a measurement in a reference waveband to obtain increased stability. When the infrared attenuation is determined only in a single waveband, this will preferably be a waveband in which lactose absorbs, as lactose has been found to be the single component showing the highest correlation to the extraneous water determination. While a determination of the amount of extraneous water could be performed using such a single wavelength infra-red determination as the only input, it would constitute a rather coarse screening only, and the inclusion of more infra-red information is highly preferred and in accordance with the philosophy of the present invention.

Higher precision of the determination of extraneous water is also obtained when, in addition to the infra-red attenuation measurement, the electrical conductivity of the sample is determined, and the quantitative assessment of the amount of any extraneous water is performed on the basis of the determination of the infra-red attenuation measurement, the determination of the electrical conductivity of the sample, and pre-determined regression coefficients derived from multivariate calibration with respect to the relationship between infrared attenuation in the at least one waveband, determined electrical conductivity and the amount of extraneous water.

In accordance with what is mentioned above, the determination (a) is preferably used in the assessment (b) without any substantial intermediate conversion to concentration values of components in the sample, and is more preferably used directly in the assessment (b) without any intermediate conversion except possibly a standardisation against water and an A/D conversion. In addition to saving the conversion steps, this direct use of the determination increases the accuracy of the assessment of extraneous water because any errors generated in the conversion steps could reappear, even to a higher extent, in the assessment.

The multivariate calibration is preferably performed using a number of milk samples the leverage of which has been increased with respect to determination of extraneous water. Although the calibration is often multi-dimensional, the leverage may be easily illustrated by a simple two-dimensional example: In this example, performing a calibration corresponds to drawing a straight line through a number of points in a two-dimensional space. The measure of quality of the calibration will then be its ability to calculate the line representing the most general axis of the collection of points (see, e.g., FIG. 5). If the points are distributed evenly in an oblong ellipse, the calibration should result in a straight line along the major axis of the ellipse. The leverage of points evenly distributed within a very oblong ellipse is increased compared with the leverage of points evenly distributed within a less oblong ellipse, as the calibration is likely to result in a line which better approximates the actual major axis of the ellipse.

The leverage of the samples used for the multivariate calibration with respect to the determination of extraneous water may be increased in several ways. One preferred method is to deliberately include extraneous water in at least one of the samples. In this way, the distribution of the samples will be expanded beyond the natural fluctuations (in the two-dimensional example, the ellipse will be more oblong). In this embodiment, it will normally be preferred to include extraneous water in a number of the samples, preferably with variation of the amount of extraneous water between these samples.

Another way of increasing the leverage of the samples is to include at least one sample which consists substantially entirely of water. In this way, at least one point, if seen in the two-dimensional illustration, is generated far away from the points of the natural samples. As this point is positioned on the ideal calibration line, again seen in the two-dimensional illustration, it will contribute to "draw" the calibration line towards the ideal direction.

A further way of increasing the leverage of the samples with respect to the determination of extraneous water is by inclusion of data manipulated to correspond to the effect of extraneous water. Thus, instead of actually generating altered samples and performing measurements on these altered samples, it is possible to manipulate data to correspond with the effect of added extraneous water and to use these manipulated data in the calibration. This manipulation may be performed by altering the infra-red attenuation values obtained from a natural sample so that they correspond to the infra-red attenuation values of the same sample now containing a certain percentage of extraneous water. While such alteration can theoretically be performed solely on the basis of calculations, it will typically be performed on the basis of previously observed changes in infra-red attenuation caused by inclusion of known amounts of extraneous water in milk samples. This method has the advantage that the calibration of the method or of the instrument can be performed solely on the basis of natural milk samples.

An additional way of increasing the leverage of the samples used for the multivariate calibration with respect to the determination of extraneous water is to define one or several of the regression coefficients prior to the multivariate calibration. Thus, instead of e.g. using a pure water sample for increasing the leverage of the samples (the distant point in the two-dimensional illustration), one or several of the regression coefficients may be taken out of the calibration and defined in advance. In the two-dimensional analogy, this may be illustrated by defining a point through which the calibration line must pass. This may be practical where the infra-red attenuation in a certain waveband is useful for determination of a certain component of the milk (such as will be described below), but where the inclusion of this waveband has been found to reduce the quality of the prediction of the extraneous water in the sample. In this situation, the regression coefficient concerning this waveband may be predefined in the calibration of the assessment of extraneous water so that the undesired effect of this waveband is eliminated. An example of this technique is seen in Example 1 herein: in addition to increasing the leverage of the calibration samples by addition of extraneous water, some of the regression coefficients have been predefined to zero, as these coefficients, if allowed to vary, have been found to adversely influence the quality of the assessment of extraneous water. An other example of increasing the leverage of the samples by predefining parameters of the calibration is by predefining the constant term of the calibration (in the Examples termed "constant"). Pre-definition of the constant parameter in the assessment of extraneous water in such a way that the assessment of pure water gives 100% extraneous water, would increase the leverage of the calibration for extraneous water in much the same way as by inclusion of a sample of pure water in the calibration.

While the above detailed description concerns the direct determination of extraneous water, it will be understood that those novel principles according to the invention which relate to the direct utilization of the infra-read attenuation and to the increase of the leverage in the calibration can also be applied to the concept of determining the freezing point depression of the milk sample, in other words the parameter which is conventionally used as an indirect indication of the concentration of any extraneous water.

Thus, one aspect of the invention relates to a method for the determination of the freezing point depression of a milk sample, the method comprising the steps of:

a) performing a determination of the infra-red attenuation of the sample in at least one waveband, b) determining the freezing point depression of the sample on the basis of the determination (a) and predetermined regression coefficients derived from multivariate calibration with respect to the relationship between infrared attenuation in the at least one waveband and the freezing point depression of the sample, the determination (a) being used in the assessment (b) without any substantial intermediate conversion to concentration values of components in the sample.

Another aspect of the invention relates to a method for determining the freezing point depression of a milk sample, the method comprising the steps of:

a) performing a determination of the infra-red attenuation of the sample in at least one waveband, b) determining the freezing point depression of the sample on the basis of the determination (a) and predetermined regression coefficients derived from multivariate calibration with respect to the relationship between infrared attenuation in the at least one waveband and the freezing point depression of the sample, the leverage of the samples used for the multivariate calibration having been increased with respect to the determination of the freezing point depression by one or several of the following measures 1)–4)

1) addition of water to at least one of the samples, 2) including, in the multivariate calibration, at least one sample which consists substantially entirely of water, 3) including, in the multivariate calibration, data manipulated to correspond with the effect of extraneous water, 4) defining one or several of the regression coefficients prior to the multivariate calibration.

With respect to the manner in which the determination and calibration are performed, the detailed explanation given above in connection with the direct determination of extraneous water also applies to the determination and calibration operations to be performed in connection with the determination of the freezing point depression, with the difference that the amount of any additional water added to the samples used for the calibration need not be known when calibrating a system for the determination of freezing point depression. Instead, when calibrating a system for the determination of freezing point depression, the freezing point depression determined on the samples used for this calibration usually is incorporated.

The electrical conductivity of the sample may be included in the prediction of the freezing point depression of the sample in the same manner as described in the context of determination of extraneous water of the sample.

In each case where an additional parameter is included in the determination, the calibration is adapted so as to also take this parameter into consideration.

The above methods for the determination of either extraneous water in a sample or the freezing point depression of the sample may advantageously be combined with the determination of the concentration of at least one component of the milk. Routine methods for determining the concentration of milk components, in particular fat and non-fat solids, are based on infrared attenuation determination. The methods of the present invention for determining extraneous water or freezing point depression are valuable supplemental determinations which can suitably be performed using the same overall type of instruments which is used for the routine determinations of the concentration of milk components. In this situation, the instruments will be equipped so that they are able to measure in the wavebands in question and optionally additionally so that they can determine the electrical conductivity of the samples.

Thus, the present invention further provides a combined method wherein, in addition to the determination of extraneous water or freezing point depression as discussed above, also the concentration of at least one milk component is determined using the determination of the infra-red attenuation of the sample in at least one waveband and predetermined regression coefficients derived from multivariate calibration with respect to the relationship between infrared attenuation in the at least one waveband and the concentration of the component in question.

The at least one milk component, the concentration of which is also determined, may typically be selected from the group consisting of fat, lactose, protein, urea, citric acid, free fatty acids, antibiotics, phosphates, somatic cells, bacteria, preservatives and casein.

In this combined method, it is often preferred that the determination of the extraneous water or the freezing point depression is performed in the same routine as the determination of the concentration of the milk component or components, which means that the calibration will normally involve determination of all required regression coefficients and will thus be performed using samples which, in addition to variation with respect to the component or components to be determined, also show variation with respect to extraneous water or freezing point depression. The variation or leverage of the samples with respect to determination of extraneous water or freezing point depression can be established in a number of ways, ranging from addition of water to some of the samples to manipulation of data, such as discussed above.

In any of the above aspects of the invention, the number of wavebands used in the determination of infra-red attenuation depends on the actual situation and on the complexity of the system, such as the number of milk components to be determined. However, it is preferred that the determination of infra-red attenuation is performed in at least 2 wavebands, such as in at least 4 wavebands, more preferably in at least 8 wavebands, such as in 8–15 wavebands. It has been conventional to perform measurement in 2 wavebands per milk component to be determined, one of the wavebands being positioned at an absorption peak of the component in question and the other waveband constituting a background or reference. However, in modern systems, this may not apply to all components as a reference may be used for more than one component. Furthermore, more than one absorption peak of a component may be used in order to perform a better determination of the concentration of this component, thus, increasing the number of wavebands used for the determination of this component.

Aspects of the present invention can be defined as methods for the establishment of the regression coefficients which are used in the above-mentioned assessments of any extraneous water in a sample or of the freezing point of a sample, in other words methods for calibrating the systems in question.

Thus, in a further aspect, the present invention provides a method for the establishment of a set of regression coefficients for use in an instrument which determines any extraneous water contained in a milk sample by determination of the infra-red attenuation of the sample in at least one waveband and quantitative assessment of the amount of any extraneous water in the sample on the basis of the determination of the infra-red attenuation and the set of regression coefficients, the method comprising performing a multivariate calibration with respect no the relationship between infrared attenuation in the at least one waveband and the amount of extraneous water using a number of milk samples the leverage of which is increased with respect to the determination of extraneous water.

The ways in which the leverage is increased are discussed in detail above.

The physical handling of one embodiment of increasing the leverage of the samples could be performed by a) obtaining a number of milk samples, b) replacing at least one sample with a sample containing a percentage A of the original milk sample and a known percentage (1-A) of extraneous water, c) performing a determination of the infra-red attenuation in the number of wavebands of the individual samples, d) performing a multivariate calibration of the instrument on the basis of the known percentage or percentages of extraneous water and the determined infra-red attenuation values of the individual samples.

In this way, samples containing from 0 to 100% water may be manufactured for use in order to increase of the leverage.

When the determination utilizes the determined electrical conductivity of the sample, the calibration may further comprise the step of:

f) after step (b) and before performing step (d) performing a determination of the electrical conductivity of the sample, and including the electrical conductivity in the multivariate calibration.

In addition to, or instead of, replacing samples with samples containing 0-100% extraneous water, at least one of the individual samples may be divided into a number of new samples and known amounts of extraneous water added to at least some of the new samples so that one sample may form the basis for a number of new samples.

Preferably, the multivariate calibration is performed using at least 5 samples, such as at least 10 samples. In many cases, 10-20 samples, such as about 15 samples, will be a suitable number; however, in other cases, at least 20 samples may be preferred in order to obtain a satisfactory calibration. The dependence of the quality of the calibration on the number of samples can be evaluated by performing a number of calibrations using a certain number of samples and calculating the standard deviation within the calibrations, and comparing the standard deviation with that of the same number of calibrations performed using a different number of samples.

The number of samples in which extraneous water should be incorporated will depend on the total number of samples, the amount of water added, and whether or not other of the above-discussed ways of increasing the leverage of the samples are used. However, it is generally preferred that extraneous water is added to at least 2 samples used for the multivariate calibration, such as at least 4 samples. It is often preferred that extraneous water has been included in at least about one third of the samples used for the multivariate calibration, and normally, extraneous water is included in about half of the calibration samples. However, it may be preferred to include extraneous water in as much as about two thirds of the samples used for the multivariate calibration.

The increase in leverage of the samples used in the calibration will depend on both the number of samples in which the leverage has been increased and on how much the overall leverage has been increased. In the case where the leverage is increased by adding extraneous water to part of the samples, it may thus be preferred that the extraneous water added corresponds to at least 0.5%, such as 1-10%, more preferably 2-8%, such as 3-6%, of the volume of the individual sample.

The assessment of the freezing point depression or the determination of any extraneous water is typically performed on raw milk samples. It is thus preferred that the samples used for the calibration are raw milk samples. As some extraneous water may be introduced due to insufficient draining of milking machines, it is preferred that the raw milk samples used in the calibration for the determination of extraneous water are samples directly as they exist after manual milking as, otherwise, these samples may contain an unknown amount of extraneous water.

A further aspect of the present invention relates to a method for establishment of a set of regression coefficients for use in an instrument which determines the freezing point depression of a milk sample by determination of the infra-red attenuation of the sample in at least one waveband and assessment of the freezing point depression of the sample on the basis of the determination of the infra-red attenuation and the set of regression coefficients, the method comprising performing a multivariate calibration with respect to the relationship between infrared attenuation in the at least one waveband and freezing point depression using a number of milk samples the leverage of which is increased with respect to the determination of freezing point depression.

Apart from the fact that in this calibration for the determination of the freezing point depression, the known parameter is the measured freezing point depression and not the amount of water added to the samples, the above-discussed ways of increasing the leverage of the samples used for the multivariate calibration and of performing the calibration also apply to this aspect.

The regression coefficients may be derived from the multivariate calibration by, e.g. a method selected from the group consisting of Partial Least Squares algorithm, Principal Component Regression, Multiple Linear Regression, and Artificial Neural Network learning, or by combinations thereof. These methods are known per se and are described in the literature.

The determination of freezing point depression of a milk sample or of the amount of extraneous water contained in the sample may be performed using an instrument comprising:

a) infra-red attenuation measuring means suited for determining the infra-red attenuation of the sample in a number of wavebands, b) a storage means capable of storing a set of regression coefficients, and c) calculating means which are adapted to calculate, on the basis of the measured infrared attenuation values and using the set of regression coefficients, the freezing point depression of the sample or the amount of extraneous water contained in the sample.

The system may additionally comprise means for determining the electrical conductivity of the sample. In this case, the calculating means should be adapted to calculate, on the basis of the measured infrared attenuation values and the electrical conductivity of the sample, and using the set of regression coefficients, the freezing point depression of the sample or the amount of extraneous water contained in the sample.

The infra-red attenuation measuring means may be of any type suitable for determining the infra-red attenuation of a liquid sample in a number of wavebands. The infra-red attenuation measuring means may comprise means for selecting and defining the individual wavebands in which infra-red attenuation is determined, such as optical filters. Alternatively, the wavebands may be defined by a stationary grating and movable and/or multiple detectors or movable grating and one or several stationary or movable detectors.

In another embodiment, at least part of the infra-red attenuation spectrum of the sample may be obtained without the use of waveband-defining means, such as when the infra-red attenuation measuring means comprise a Fourier transform interferometer for obtaining the infra-red attenuation values.

Interaction between the sample and the infra-red light may be obtained in a number of ways. One way of obtaining this interaction is by using an ATR technique, wherein the light travels in a crystal and on to a boundary between the crystal and the sample, whereby the light interacts with the sample.

Another way of having the infra-red light interact with the sample is using a transmission technique. In this technique, the light is transmitted through the sample. This may be performed when at least part of the sample is held by a cuvette through which infra-red light is transmitted during determination of infra-red attenuation. In order to be able to detect light transmitted through the sample, the thickness of the cuvette in the direction of the light should be kept sufficiently low. This thickness is preferably at the most 200 μm, such as at the most 100 μm, more preferably at the most 50 μm, and in certain cases even thinner, such as at the most 25 μm.

The storage means of the system may be any known kind of storage means for this type of parameters, such as hard-disc, RAM, ROM, floppy-disk, etc. The calculation means may also be of any suitable type, such as microprocessor, neural network, etc.

The means for determining the electrical conductivity of the sample may be of a number of types; however, in the presently preferred embodiment, this means comprises a number of electrodes positioned in electrical contact with the sample during determination of the electrical conductivity. The electrodes may suitably constitute part of at least the inner surface of a conduit through which the sample is passed.

As the position and spatial arrangement of the electrodes will affect the measurement of the electrical conductivity, the electrodes are preferably formed on the inner side of the liquid conduit in such a manner so that they are spatially separated in the direction of flow of the liquid in the conduit. This arrangement gives a simple and controllable structure of the electrodes.

Several methods exist for the determination of the electrical conductivity of a liquid sample. Typically, a current is conducted through the liquid and the voltage generated across part of the sample is measured; the determination of the electrical conductivity of the sample is based on the voltage, the current, and a geometry factor depending on the arrangement of the electrodes.

At present, it is preferred that the means for determining the electrical conductivity of the sample contains at least 4 electrodes for the determination of the electrical conductivity of the sample.

In one preferred embodiment of the means for determination of the electrical conductivity, a total of 4 electrodes are positioned in the liquid conduit in the direction of flow, the two middle electrodes being connected to an instrument for determining voltage, a current being passed through the liquid in the conduit by feeding opposite voltages to the two outer electrodes.

In order to avoid leakage of current into the liquid system of the instrument, two additional electrodes may be positioned on the outer sides of the 4 electrodes, seen in the direction of flow in the conduit, and a voltage may be fed to each of these end electrodes, this voltage being substantially the same as that of the adjacent outer electrode.

In order to avoid electrolysis and polarization at the surfaces of the electrodes, the voltages fed to the electrodes may be ac voltages.

BRIEF DESCRIPTION OF THE DRAWING

In the following, a preferred embodiment of the present invention will be described by way of examples and with reference to the drawing, wherein.

DESCRIPTION OF THE PREFERRED EMBODIMENTS

EXAMPLE 1

Calibration of Freezing Point Depression in Milk, Using Natural Milk Samples and Samples with Extraneous Water Calibration samples The sample material used in this example were 242 samples divided into two groups. The first group, referred to as "Natural samples", consisted of 148 bulk-milk samples, and the second group, referred to as "Extraneus water samples", consisted of 47 bulk-milk samples, which were divided into two portions, and where to one portion of each of these samples water was added, amounting to 3 or 6% extraneous water, giving a total of 94 Extraneous water samples.

Figure 1:
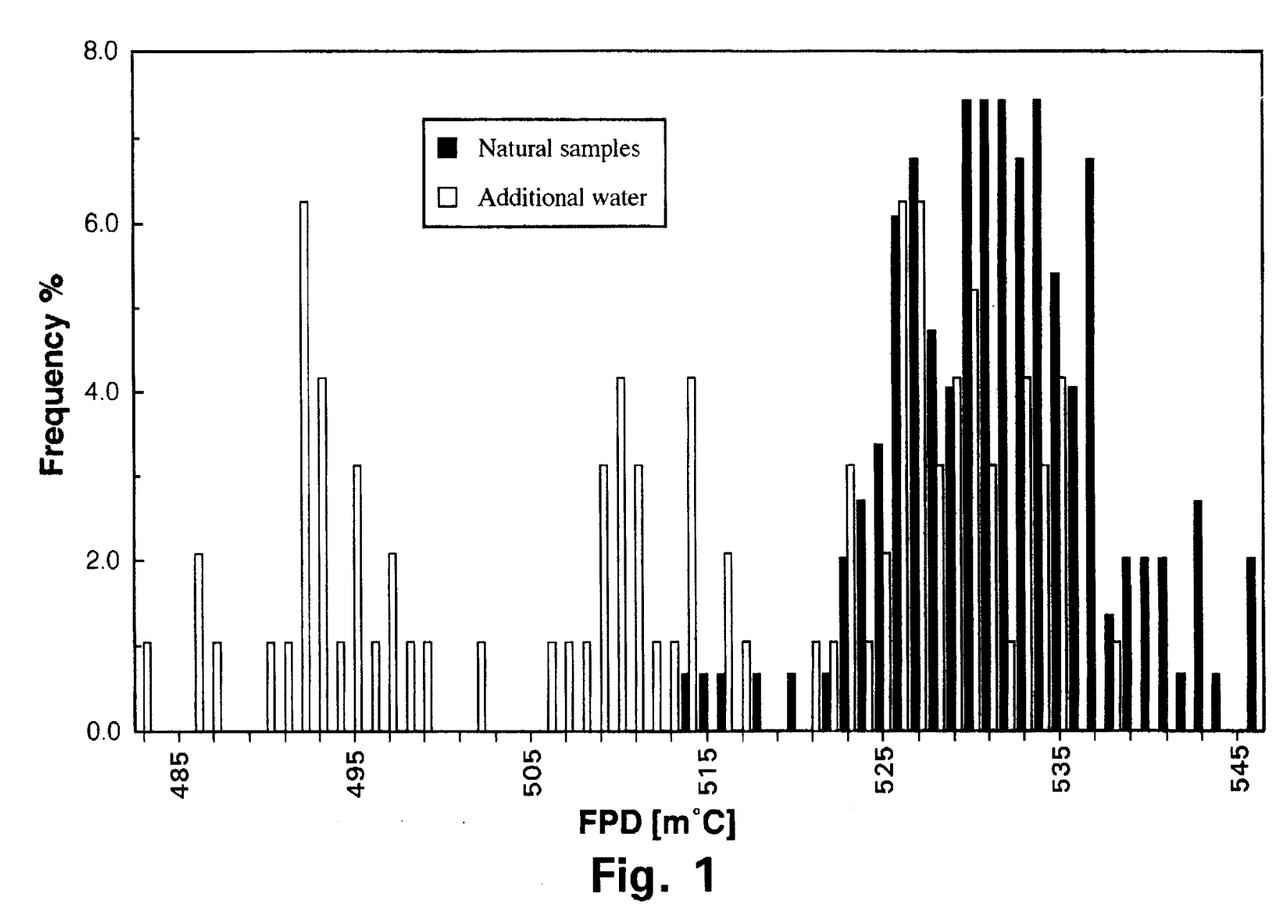
FIG. 1 illustrates the distribution of the measured freezing point depression (FPD) of two sample groups.

The samples were collected during a period of 10 weeks. Portions of each of the 242 samples was analyzed by reference method for Freezing Point Depression on a Cryoscope (Advanced Cryometric Milk Cryoscope - CII, Advanced Instruments Inc. Massachusets USA) and a portion of the samples was measured on MilkoScan 4000 (Foss Electric, Hillerød Denmark) in triplicate measurement giving a total of 726 measurements. From the MilkoScan 4000, data from nine IR filters and a conductivity cell was collected. FIG. 1 shows the distribution of the measured Freezing Point Depression results in the two sample groups where the dark columns represent Natural samples and the white columns represent Extraneous water samples. Triplicate measurements are performed so as to be able to evaluate the repeatability of the method.

Calibration according to the invention 20 subsets consisting of 10, 20, 40 and 80 samples (30, 60 120 and 240 measurements on the MilkoScan 4000 and a total of 80 subsets) were randomly selected from the two sample groups Natural samples (148 samples) and Extraneous water (94 samples), and subjected to Partial Least Squares calibration as described, e.g. in "Multivariate Calibration" by Harald Martens and Tormod Næs, John Wiley & Sons, London, 1989, pp 116–125.

The prediction of the resulting calibrations was nested on the group of Natural samples. When the calibration was based on samples from this group, those samples were excluded before prediction. The ability to predict the Freezing Point Depression was estimated by the mean value of the Standard Error of Prediction (SEP m° C.) describing the mean value for the 20 calibrations performed on the actual number of samples, and its standard deviation ($SD_{SEP}$) describing the deviation between the 20 calibrations performed in each subset. The result of the prediction is given in the following table.

| Number of calibration samples | SEP m °C. Natural samples | $SD_{SEP}$ Natural samples | SEP m °C. Extraneous water | $SD_{SEP}$ Extraneous water |
|---|---|---|---|---|
| 10 | 5.86 | 2.31 | 4.60 | 0.58 |
| 20 | 3.58 | 0.58 | 3.39 | 0.29 |
| 40 | 3.25 | 0.39 | 3.15 | 0.17 |
| 80 | 2.98 | 0.31 | 3.10 | 0.09 |

The resulting regression equations for Freezing Point Depression, consisting of a set of terms comprising a regression coefficient as found by Partial Least Squares regression, was estimated using all samples in the two groups. The resulting regression equations are given in the following table.

| Signal | Wavelength μm | Natural samples | Extraneous water |
|---|---|---|---|
| IR-01 | 6.70 | 0 | 0 |
| IR-02 | 6.50 | −572.5 | −434.0 |
| IR-03 | 7.20 | 124.0 | 249.1 |
| IR-04 | 6.83 | 1844.4 | 2042.1 |
| IR-05 | 7.70 | −681.6 | −1247.2 |
| IR-06 | 3.560 | 1461.9 | 469.2 |
| IR-07 | 3.505 | −724.2 | −205.0 |
| IR-08 | 5.58 | −3485.2 | −947.21 |
| IR-09 | 9.50 | 194.9 | 360.86 |
| Conductivity | — | 0.0949 | 0.1041 |
| Constant | — | −76.95 | −110.43 |

Figure 2:
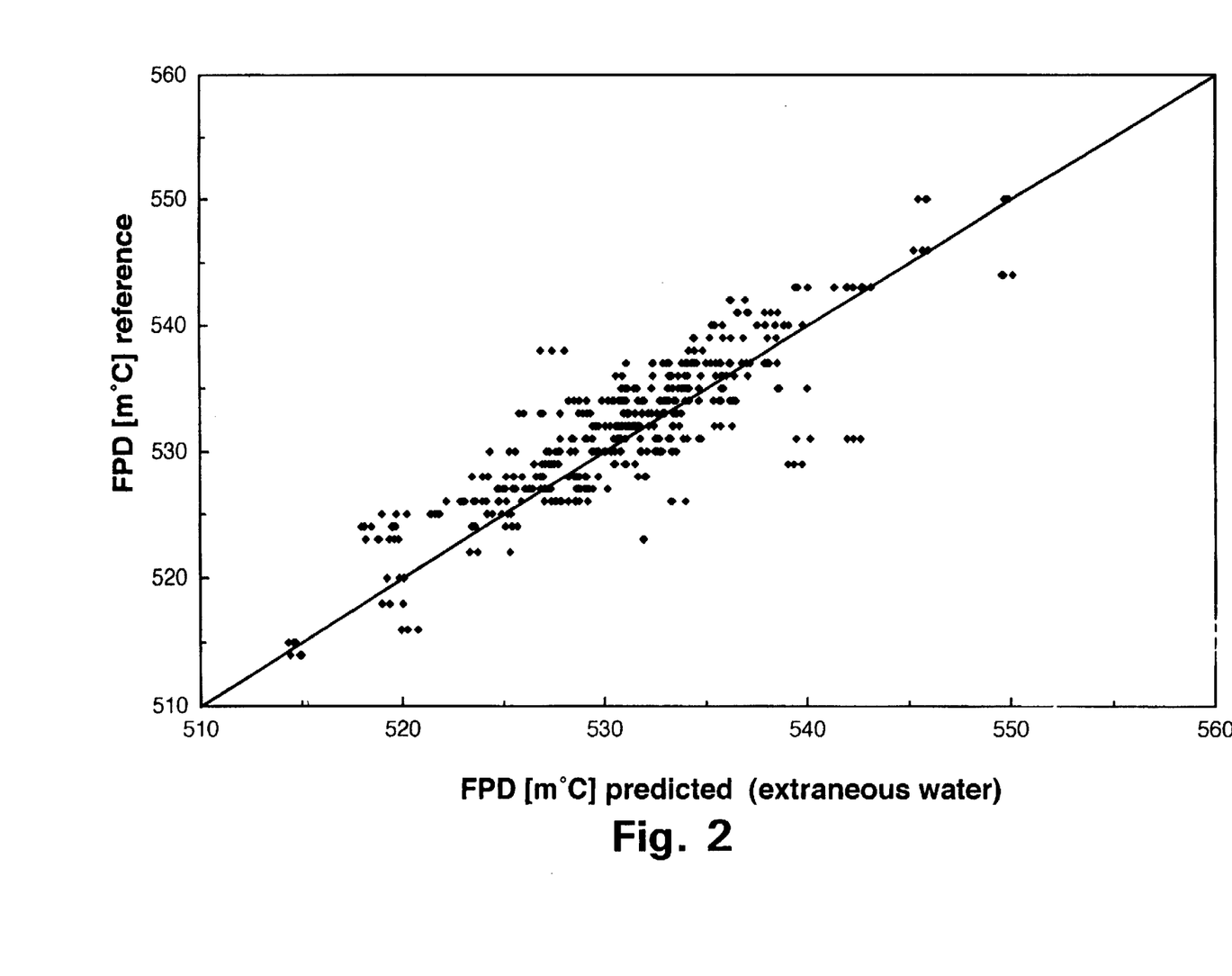
FIG. 2 illustrates the measured FPD versus the predicted FPD based on a calibration using samples with extraneous water.

FIG. 2 shows a graph of the Freezing Point Depression versus the predicted Freezing Point Depression, from a calibration based on data from samples with extraneous water. The Standard Error of Prediction is estimated to 3.15 m° C., and the repeatability of the MilkoScan prediction is about 0.51 m° C. From this figure it is seen that the measurements are grouped in groups of three points. The three points in each group concern the triplicate measurement of a single sample. The spread of the points in the groups, thus, illustrate the repeatability of the method.

Conclusion

The results in this Example demonstrate that it is possible to obtain a calibration based on IR-attenuation data and conductivity as measured by the MilkoScan 4000, and a Cryoscope-determination of the freezing point depression, for the prediction of the Freezing Point Depression in natural milk samples, using samples where extraneous water has been added to the calibration samples.

It was found that a calibration created on the basis of data from samples with extraneous water resulted in similar or better average predictability, expressed as Standard Error of Prediction, as a calibration created on the basis of data from natural samples. It was also found that a calibration on the basis of data from samples containing extraneous water resulted in a calibration which showed better stability, expressed as the variation in the Standard Error of Prediction, than calibrations created on the basis of data from natural samples.

EXAMPLE 2

Direct Prediction of Extraneous Water in Milk Using IR-absorption and Conductivity Calibration samples The sample material used in this Example corresponds to the samples used in Example 1. In this Example, however, only the samples in the Extraneous water group were used in the calibration.

As in Example 1, portions of each of the 242 samples was measured on a MilkoScan 4000 (Foss Electric, Hillerød, Denmark) in triplicate measurement giving a total of 726 measurements, and data from nine IR filters and a conductivity cell was collected.

Calibration according to the invention 20 subsets now consisting of 10, 20, 40 and 60 samples (30, 60, 120 and 180 measurements on the MilkoScan 4000) were randomly selected from the Extraneous water samples (94 samples), and subjected to Partial Least Squares calibration as described in Example 1.

The prediction of the resulting calibrations was tested on the samples from the group of Extraneous water samples which were not included in the calibration. The ability to predict the amount of extraneous water was estimated by the mean value of the Standard Error of Prediction (SEP %) and its standard deviation ($SD_{SEP}$). The result of the prediction is given in the following table.

| Number of calibration samples | SEP % | $SD_{SEP}$ |
|---|---|---|
| 10 | 0.73 | 0.14 |
| 20 | 0.63 | 0.07 |
| 30 | 0.58 | 0.03 |
| 40 | 0.55 | 0.05 |
| 60 | 0.53 | 0.05 |

The resulting regression equations for extraneous water, consisting of a set of terms comprising a regression coefficient as found by Partial Least Squares regression, was estimated using the entire calibration group of Extraneous water samples. The resulting regression equations are given in the following table which shows firstly the calibration with the optimal selection of filters and secondly the best calibration using the same IR-wavelengths as the Freezing Point Depression calibration in Example 1.

| Signal | Wavelength µm | Extraneous Water | "FPD signals" |
|---|---|---|---|
| IR-01 | 6.70 | 92.05 | 0 |
| IR-02 | 6.50 | −2.69 | 4.17 |
| IR-03 | 7.20 | −11.09 | −14.08 |
| IR-04 | 6.83 | −63.51 | −10.95 |
| IR-05 | 7.70 | −8.636 | −8.43 |
| IR-06 | 3.56 | −50.34 | −13.57 |
| IR-07 | 3.50 | 0 | −46.43 |
| IR-08 | 5.58 | 60.42 | 6.88 |
| IR-09 | 9.50 | −57.75 | −57.08 |
| Conductivity | — | −.0185 | −0.01 |
| Constant | — | 101.74 | 102.15 |

Results

Figure 3:
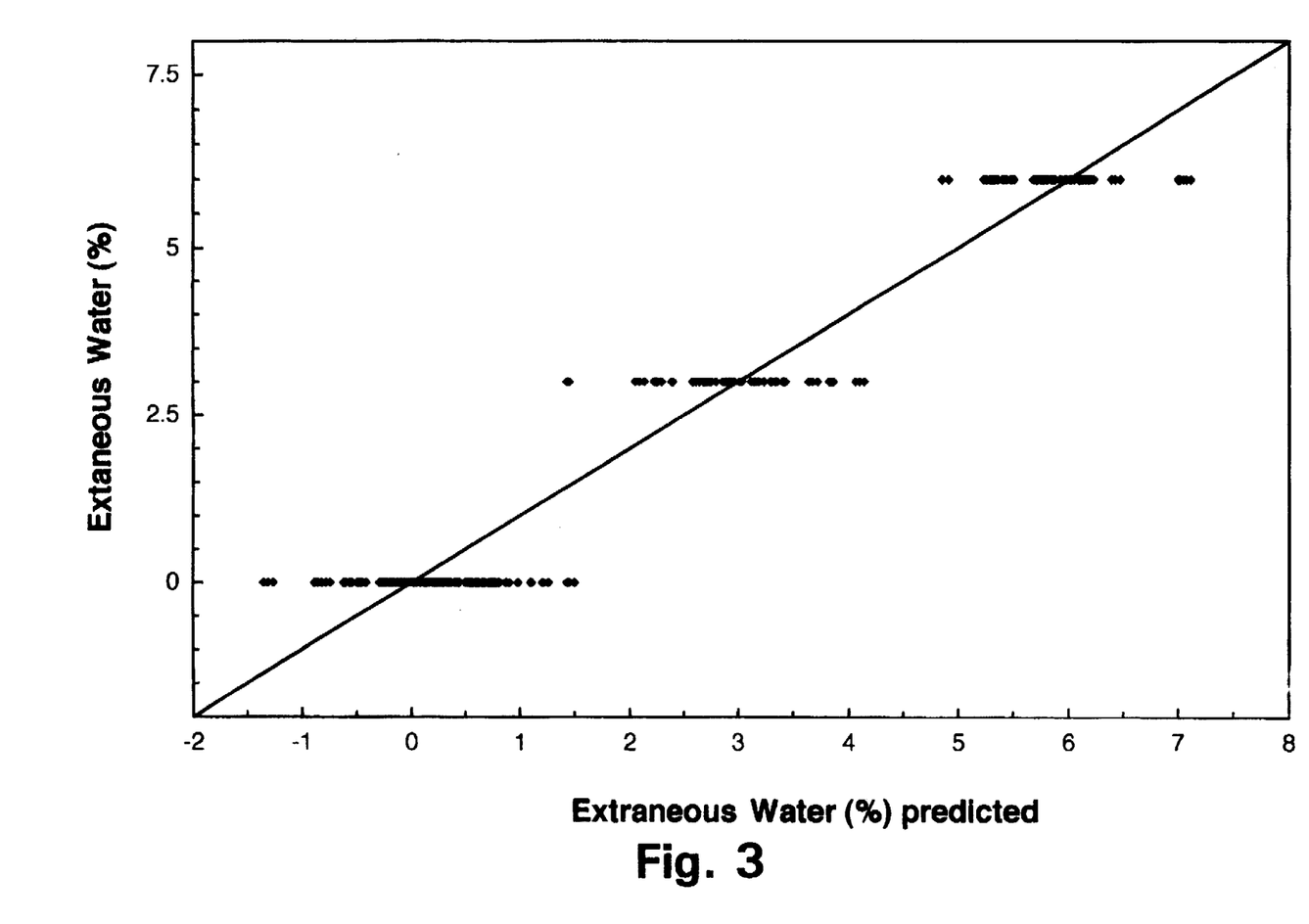
FIG. 3 illustrates the predicted extraneous water in the samples versus the extraneous water added to the samples.

FIG. 3 shows a graph of the actual amount of extraneous water versus the predicted extraneous water, from a calibration based on data from the group of Extraneous water samples. The Standard Error of Prediction is estimated to be 0.57% extraneous water, and the repeatability of the MilkoScan prediction was estimated to be 0.04% extraneous water.

Figure 4:
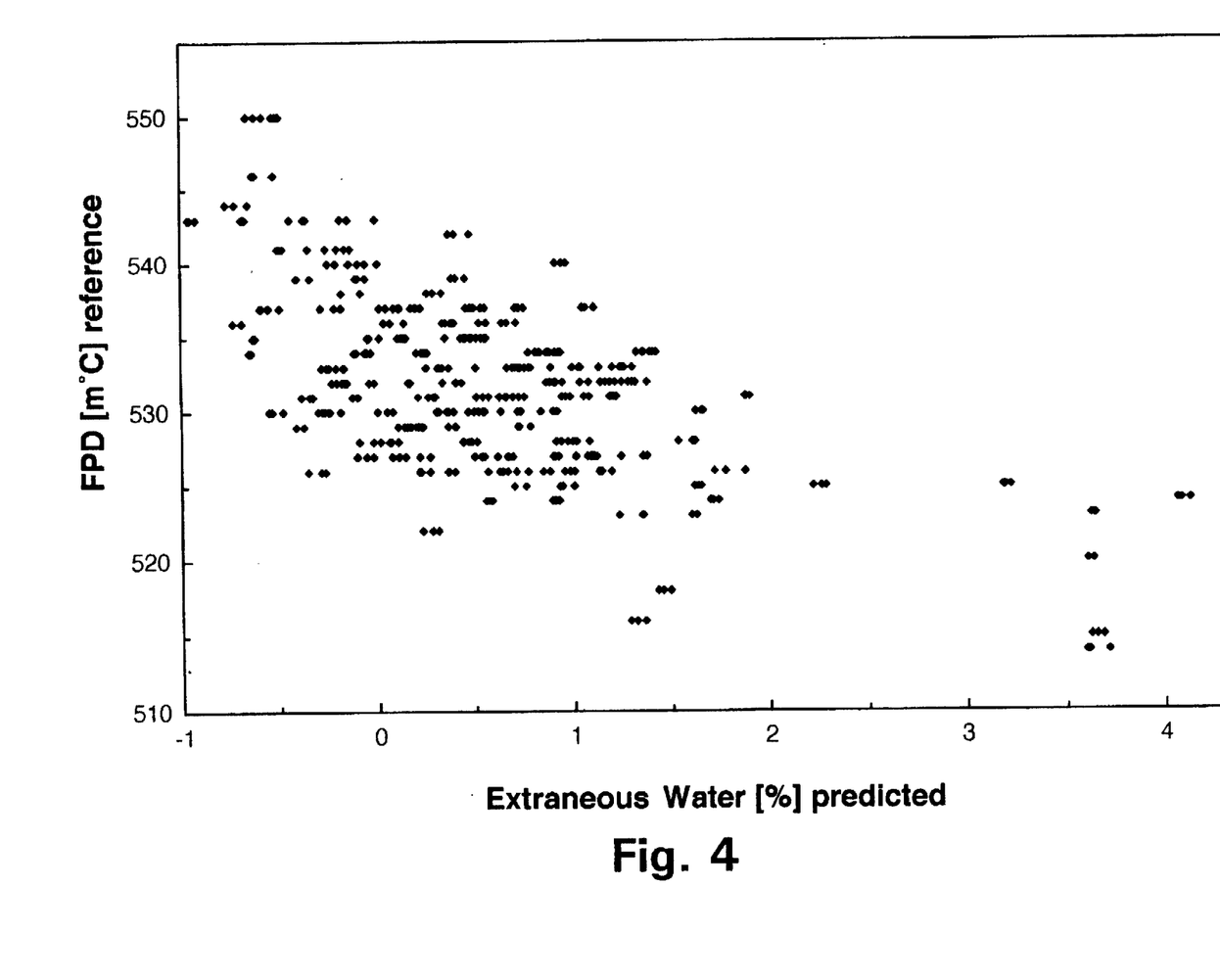
FIG. 4 illustrates the predicted amount of extraneous water versus the measured FPD of the test sample group.

When the resulting regression coefficients for extraneous water are compared with the results from Example 1, it is obvious that the calibrations are different, both regarding the optimum selection of IR-wavelengths, but also when a calibration using the same IR-wavelengths is considered. This difference is shown in FIG. 4 which shows a graph of the measured Freezing Point Depression of the test sample group versus the predicted extraneous water. As described with reference to FIG. 2, the points are grouped in groups of three from the triplicate measurements of the samples. Again this illustrates the repeatability of the method.

The samples used in this Example are non authentic milk samples (directly from the cow by manual milking), whereby some of them will contain an initial unknown amount of extraneous water. Assuming validity of the extraneous water calibration, the initial amount of extraneous water will contribute to the Standard Error of Prediction. It is therefore of interest to investigate the recovery of extraneous water as found by the prediction model, defined as the difference between the predicted result for the initial sample and the prediction for the same sample after the addition of known amount of extraneous water. This means, that the absolute amount of extraneous water in the samples is not known—only the relative value positively added as described. By investigating the recovery of extraneous water, it will be investigated whether the method is able to re-identify the relative amount of extraneous water.

Figure 5:
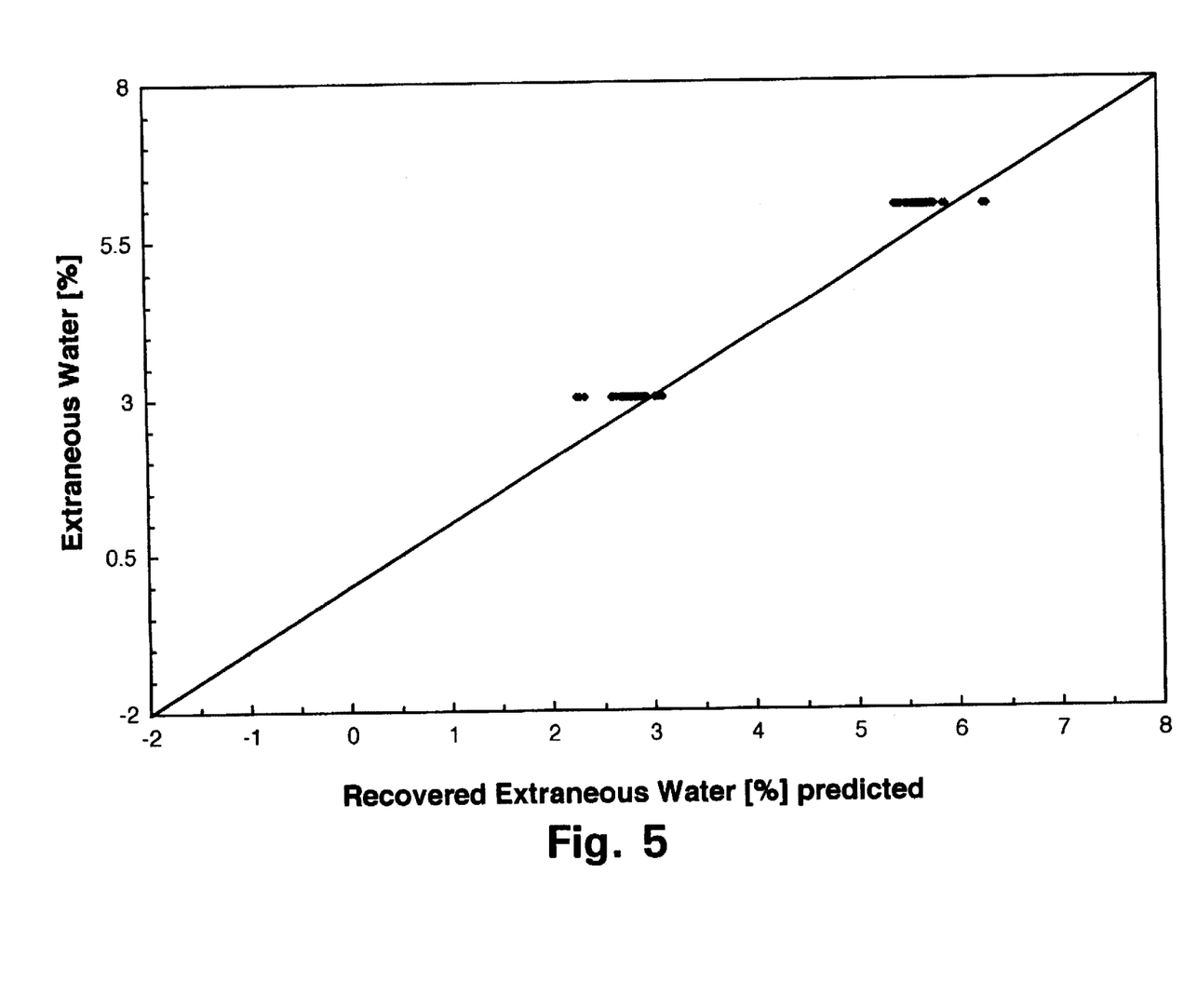
FIG. 5 illustrates the actual amount of extraneous water added to the samples versus the amount of recovered extraneous water, FIG. 6 diagrammatically illustrates the system according to the invention.

The prediction of recovered extraneous water is shown in FIG. 5. The result of the recovered Extraneous Water suggests an error in recovery of about 0.15% extraneous water with a repeatability error of about 0.04% extraneous water.

This may be illustrated by returning to FIG. 3. In this figure it is seen that the predicted values of extraneous water is spread over a certain area. However, when looking at the distribution of the measurements, it is seen that a number of groups are offset from the calibration line at both 0, 3, and 6% extraneous water. It is contemplated that these offset samples contained extraneous water from the beginning, whereby, if manually milked samples were used, this spread of predicted values would be smaller in all three groups, thus improving the calibration and the prediction of extraneous water in the samples.

Figure 6:
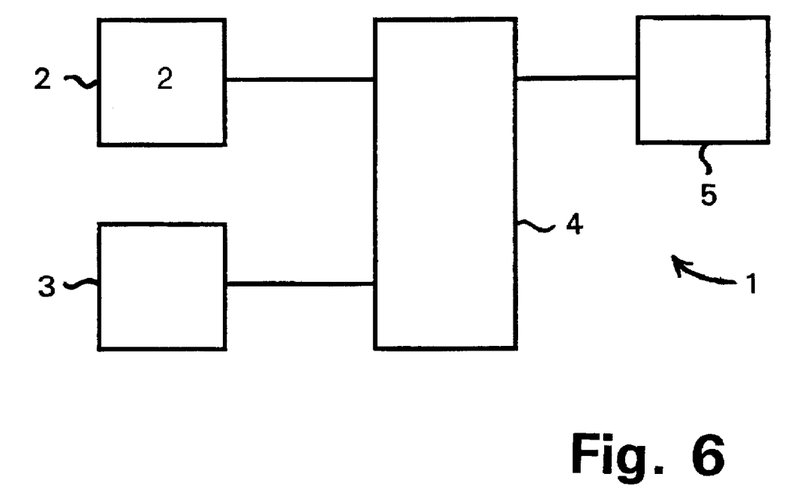

FIG. 6 diagrammatically illustrates a preferred embodiment of the system 1 according to the invention. The infra-red attenuation measuring means 2 may be of any type which is able to determine the light attenuation of the sample in at least one waveband in the infra-red region. At present, infra-red attenuation measuring means in which optical filters are used to define the wavebands are preferred, however, FTIR instruments are highly suited for this use as the whole of the infra-red absorption spectrum of the sample may be obtained in one process. When determining the infra-red attenuation of a sample, infrared light from a light source may be transmitted through the sample and a filter, for defining the waveband in which the attenuation is to be determined, and further onto a light detector. In this type of instrument, the sample is contained in a cuvette which is so thin that the infra-red light is able to pass without total attenuation, but where it is still possible to introduce and remove the sample. The cuvette should be made of a material, such as $CaF_2$, which allows the infra-red light to pass without extreme attenuation.

If the signal/noise ratio is to be elevated, the light transmitted through the sample may be turned on and off (chopped) so as to enable the use of lock-in detection. This chopping may be obtained either by introducing a chopper for that purpose or by, e.g. rotating a wheel holding the filters. In this way, when the light is not transmitted through a filter, but instead is shone onto the filter wheel, the light is turned off, contrary to the situation where the light is transmitted through a filter, where the light is, of course, turned on. This method has a number of advantages, such as the exclusion of the chopper.

The means 3 for determining the electrical conductivity of the sample may also be of any type able to determine the electrical conductivity of a liquid sample. However, as problems may arise as to fouling of the interior surfaces holding the liquid sample in the means 3, and polarization effects and electrolysis may occur in the sample, the electrical conductivity measuring means shown in FIG. 7 is presently preferred.

The determined infra-red attenuation values for the individual wavebands and the value for the electrical conductivity of the sample are transmitted to calculation means 4. On the background of these values and are stored in storing means 5, the calculation means is able to determine the amount of extraneous water in the sample or the freezing point depression of the sample.

The parameters stored in the storing means 5 are generated on the background of a calibration. These parameters will depend on the actual measurement to be performed (FPD or extraneous water) and on the actual system used. Methods for performing these calibrations is described earlier.

Figure 7:
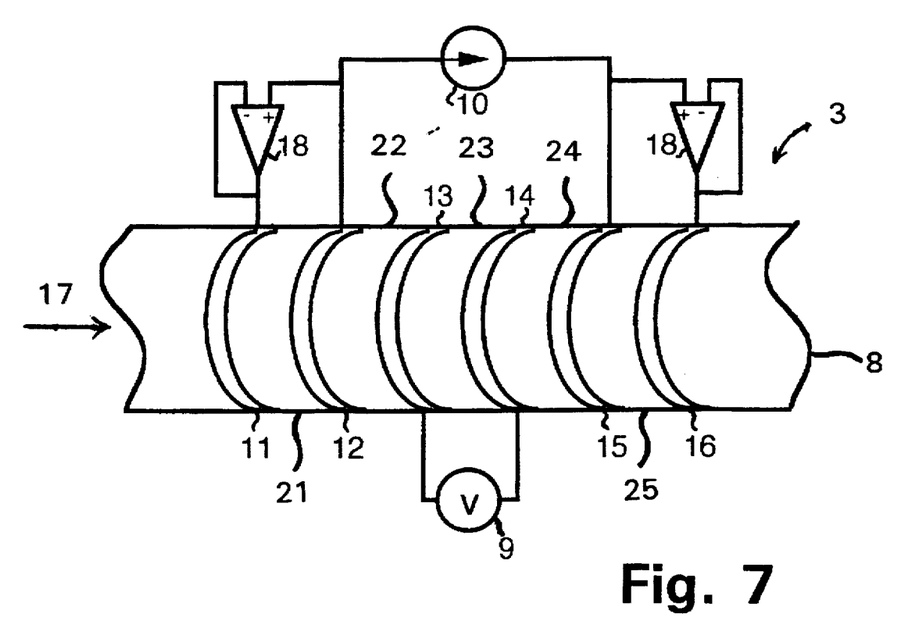
FIG. 7 illustrates a preferred embodiment of the electrical conductivity measuring means according to the invention.

FIG. 7 illustrates a preferred embodiment of the electrical conductivity measuring means 3 of the preferred system of the invention.

In this means 3, the liquid sample is held by a liquid conduit 8 through which, the liquid sample can flow. In the preferred embodiment 6 electrodes 11, 12, 13, 14, 15, and 16 are used; these electrodes are spatially separated in the direction of flow of the liquid sample (see arrow 17).

The electrodes 11–16, made of e.g. stainless steel, which are in direct electrical contact with the sample in the conduit 8, are shaped as circular electrodes, having thicknesses of e.g. 1, 1, 0.1, 0.1, 1, and 1 mm, respectively, which together with a number of electrically non-conducting separation means 21–25, e.g. made of plastics and having thicknesses of e.g. 1, 3, 3, 3, and 1 mm, respectively, constitute the conduit 8. The electrodes 11–16 and the separating means 21–25 preferably have the same inner diameter, such as 1.5 mm, so as to obtain a smooth inner surface of the conduit 8 and thus to reduce the possibility of sedimentation therein. A smooth conduit 8 also has the advantage that it results is a homogeneous electrical field in the sample. To ensure that the conduit 8 does not leak the sample, the separation means 21–25 and the electrodes 11–16 may be assembled using O-rings as known per se.

The two middle electrodes 13, 14 are connected to a voltage-meter 9. The two adjacent electrodes 12, 15 are connected to a current supply 10, whereby a current is transmitted through the part of the sample situated in the conduit 8 between the electrodes 12 and 15. The voltage across the electrodes 13 and 14 will thereby give an indication of the electrical conductivity of the sample in the conduit 8.

In this way, the electrical conductivity of the sample may be determined from the voltage difference between the electrodes 13 and 14, the size of the current fed by the electrodes 12 and 15, and a geometry factor, which may be determined on the basis of a suitable calibration of the electrical conductivity measuring means.

When using four electrodes in this configuration, the means 3 is less dependent on fouling of the electrodes and on polarization effects. Furthermore, if alternating current is fed to the electrodes 12, 15, electrolysis and polarization at the surfaces of these electrodes is eliminated.

Two additional electrodes 11, 16 are positioned adjacent to the current-feeding electrodes 12, 15. These additional electrodes are fed with the same potential as the adjacent electrodes 12, 15, respectively. In this way, no current is leaked from the means 3.

In the present embodiment, the potential fed to the additional electrodes 11, 16 is generated by operational amplifiers 18 which are connected as "voltage-followers" following the potential of each of the electrodes 12 or 15. In this way, the potential of the electrodes 12 and 15 are not altered to any significant degree by the additional electrodes 11 and 16 following the potential of electrodes.

Preferably, the means 3 for measuring the electrical conductivity of the sample is thermostated to within 0.1° C. of a given constant temperature, such as 42° C., as the electrical conductivity of milk samples depends on the temperature thereof.

As also the infra-red absorption of milk samples depends on temperature, also the cuvette in which the milk sample interacts with the infra-red light is thermostated. Thus, it may be advantageous no position the means 2 and 3 adjacent to each other so as to reduce the number of places in the system, wherein strict thermostating is required.

We claim:

1. A method for quantitatively assessing the amount of any extraneous water contained in a milk sample, the method comprising the steps of:
   a) performing a determination of the infrared attenuation of the sample in at least one waveband,
   b) quantitatively assessing the amount of any extraneous water in the sample on the basis of the determination (a) and pre-determined regression coefficients derived from multivariate calibration with respect to the relationship between infrared attenuation in the at least one waveband and the amount of extraneous water.

2. A method according to claim 1, wherein
   c) the electrical conductivity of the sample is determined, and wherein quantitative assessment of the amount of any extraneous water is performed on the basis of the determination (a), the determination (c), and pre-determined regression coefficients derived from multivariate calibration with respect to the relationship between infrared attenuation in the at least one waveband, determined electrical conductivity and the amount of extraneous water.

3. A method according to claim 1, wherein the determination (a) is used in the assessment (b) without any intermediate conversion to concentration values of components in the sample.

4. A method according to claim 1, wherein the determination (a) is used directly in the assessment (b) without any intermediate conversion except a standardization against water and an Analogue-to-Digital conversion.

5. A method according to claim 1, wherein the determination (a) is used directly in the assessment (b) without any intermediate conversion.

6. A method according to claim 1, wherein the leverage of the samples used for the multivariate calibration has been increased with respect to the determination of extraneous water by inclusion of extraneous water in at least one of the samples.

7. A method according to claim 6, wherein at least one of the samples used for the multivariate calibration consists substantially entirely of water.

8. A method according to claim 1, wherein the leverage of the samples used for the multivariate calibration has been increased with respect to the determination of extraneous water by inclusion of data manipulated to correspond with the effect of extraneous water.

9. A method according to claim 1, wherein the leverage of the samples used for the multivariate calibration has been increased with respect to the determination of extraneous water by defining one or several of the regression coefficients prior to the multivariate calibration.

10. A method for determining the freezing point depression of a milk sample, the method comprising the steps of:
    a) performing a determination of the infrared attenuation of the sample in at least one waveband,
    b) determining the freezing point depression of the sample on the basis of the determination (a) and pre-determined regression coefficients derived from multivariate calibration with respect to the relationship between infrared attenuation in the at least one waveband and the freezing point depression of the sample, the determination (a) being used in the assessment (b) without any intermediate conversation to concentration values of components in the sample.

11. A method according to claim 8, wherein the determination (a) is used directly in the assessment (b) without any intermediate conversion except an Analogue-to-Digital conversion.

12. A method according to claim 8, wherein the determination (a) is used directly in the assessment (b) without any intermediate conversion.

13. A method according to claim 10, for determining the freezing point depression of a milk sample, the method comprising the steps of:
    a) performing a determination of the infrared attenuation of the sample in at least one waveband,
    b) determining the freezing point depression of the sample on the basis of the determination (a) and pre-determined regression coefficients derived from multivariate calibration with respect to the relationship between infrared attenuation in the at least one waveband and the freezing point depression of the sample, the leverage of the samples used for the multivariate calibration having been increased with respect to the determination of the freezing point depression by one or several of the following measures 1)–4)

1) addition of water to at least one of the samples,
2) including, in the multivariate calibration, at least one sample which consists substantially entirely of water,
3) including, in the multivariate calibration, data manipulated to correspond with the effect of extraneous water,
4) defining one or several of the regression coefficients prior to the multivariate calibration.

14. A method according to claim 10, wherein
c) the electrical conductivity of the sample is determined, and wherein the determination of the freezing point depression of the sample is performed on the basis of the determination (a), the determination (c), and pre-determined regression coefficients derived from multivariate calibration with respect to the relationship between infrared attenuation in the at least one waveband, determined electrical conductivity and freezing point depression.

15. A method according to claim 10, wherein the determination of the infrared attenuation is performed in at least one waveband in which lactose absorbs.

16. A method according to claim 10, wherein the concentration of at least one milk component is determined using the determination (a) and pre-determined regression coefficients derived from multivariate calibration with respect to the relationship between infrared attenuation in the at least one waveband and the concentration of the at least one component in question.

17. A method according to claim 16, wherein the at least one milk component is selected from the group consisting of fat, carbohydrates, such as lactose, protein, urea, citric acid, free fatty acids, antibiotics, phosphates, somatic cells, bacteria, preservatives and casein.

18. A method according to claim 10, wherein the determination of infrared attenuation is performed in at least 2 wavebands.

19. A method for the establishment of a set of regression coefficients for use in an instrument which determines any extraneous water contained in a milk sample by determination of the infrared attenuation of the sample in at least one waveband and quantitative assessment of the amount of any extraneous water in the sample on the basis of the determination of the infrared attenuation and the set of regression coefficients, the method comprising performing a multivariate calibration with respect to the relationship between infrared attenuation in the at least one waveband and the amount of extraneous water using a number of milk samples the leverage of which is increased with respect to the determination of extraneous water.

20. A method according to claim 19, wherein the leverage of the samples used for the multivariate calibration is increased with respect to the determination of extraneous water by inclusion of extraneous water in at least one of the samples.

21. A method according to claim 20, wherein at least one of the individual samples is divided into a number of new samples, and known amounts of extraneous water is added to at least some of the new samples.

22. A method according to claim 20, wherein at least one of the samples used for the multivariate calibration consists substantially entirely of water.

23. A method according to claim 19, wherein the leverage of the samples used for the multivariate calibration is increased with respect to the determination of extraneous water by inclusion of data manipulated to correspond with the effect of extraneous water.

24. A method according to claim 19, wherein the leverage of the samples used for the multivariate calibration is increased with respect to the determination of extraneous water by defining one or several of the regression coefficients prior to the multivariate calibration.

25. A method according to claim 19, wherein the multivariate calibration is performed using at least 5 samples.

26. A method according to claim 20, wherein extraneous water is added to at least 2 samples used for the multivariate calibration.

27. A method according to claim 20, wherein extraneous water is included in at least about one third of the samples used for the multivariate calibration.

28. A method according to claim 20, wherein the amount of extraneous water added corresponds to at least 0.5% of the volume of the individual sample.

29. A method according to claim 19, wherein the milk samples used for the establishment of the set of regression coefficients are raw milk samples.

30. A method according to claim 29, wherein the milk samples are raw milk samples directly as they exist after manual milking.

31. A method for the establishment of a set of regression coefficients for use in an instrument which determines the freezing point depression of a milk sample by determination of the infrared attenuation of the sample in at least one waveband and assessment of the freezing point depression of the sample on the basis of the determination of the infrared attenuation and the set of regression coefficients, the method comprising performing a multivariate calibration with respect to the relationship between infrared attenuation in the at least one waveband and freezing point depression using a number of milk samples the leverage of which is increased with respect to the determination of freezing point depression.

32. A method according to claim 31, wherein the leverage of the samples used for the multivariate calibration is increased with respect to the determination of freezing point depression by inclusion of additional water to at least one of the samples.

33. A method according to claim 32, wherein at least one of the samples used for the multivariate calibration consists substantially entirely of water.

34. A method according to claim 31, wherein the leverage of the samples used for the multivariate calibration is increased with respect to the determination of freezing point depression by inclusion of data manipulated to correspond with the effect of added water.

35. A method according to claim 31, wherein the leverage of the samples used for the multivariate calibration is increased with respect to the determination of freezing point depression by defining one or several of the regression coefficients prior to the multivariate calibration.

36. A method according to claim 31, wherein the calibration is performed by
a) obtaining a number of milk samples,
b) replacing at least one sample with a sample containing additional water,
c) performing a determination of the freezing point depression,
d) performing a determination of the infrared attenuation in the number of wavebands of the individual samples, and
e) performing a multivariate calibration of the instrument on the basis of the known freezing point depression and the determined infrared attenuation values of the individual samples.

37. A method according to claim 36, further comprising the step of:

f) after step (b) and before performing step (e) performing a determination of the electrical conductivity of the sample, and including the electrical conductivity in the multivariate calibration.

38. A method according to claim 36, wherein at least one of the individual samples is divided into a number of new samples, and varying amounts of water are added to at least some of the new samples.

39. A method according to claim 31, wherein the multivariate calibration is performed using at least 5 samples.

40. A method according to claim 32, wherein water is added to at least 2 samples used for the multivariate calibration.

41. A method according to claim 32, wherein water is added to substantially one third of the samples used for the multivariate calibration.

42. A method according to claim 30, wherein the amount of water added corresponds to at least 0.5% of the volume of the individual sample.

43. A method according to claim 10, wherein the multivariate calibration is performed by a method selected from the group consisting of Partial Least Squares algorithm, Principal Component Regression, Multiple Linear Regression, and Artificial Neural Network learning, or by combinations thereof.

44. A method according to claim 1, wherein the multivariate calibration is performed by a method selected from the group consisting of Partial Least Squares algorithm, Principal Component Regression, Multiple Linear Regression, and Artificial Neural Network learning, or by combinations thereof.

45. A method according to claim 20, wherein the multivariate calibration is performed by a method selected from the group consisting of Partial Least Squares algorithm, Principal Component Regression, Multiple Linear Regression, and Artificial Neural Network learning, or by combinations thereof.

46. A method according to claim 31, wherein the multivariate calibration is performed by a method selected from the group consisting of Partial Least Squares algorithm, Principal Component Regression, Multiple Linear Regression, and Artificial Neural Network learning, or by combinations thereof.

47. A method according to claim 1, wherein the determination of the infrared attenuation is performed in at least one waveband in which lactose absorbs.

48. A method according to claim 1, wherein the concentration of at least one milk component is determined using the determination (a) and pre-determined regression coefficients derived from multivariate calibration with respect to the relationship between infrared attenuation in the at least one waveband and the concentration of the at least one component in question.

49. A method according to claim 48, wherein the at least one milk component is selected from the group consisting of fat, carbohydrates, such as lactose, protein, urea, citric acid, free fatty acids, antibiotics, phosphates, somatic cells, bacteria, preservatives and casein.

50. A method according to claim 1, wherein the determination of infrared attenuation is performed in at least 2 wavebands.

* * * * *

UNITED STATES PATENT AND TRADEMARK OFFICE
CERTIFICATE OF CORRECTION

PATENT NO. : 5,739,034
DATED : April 14, 1998
INVENTOR(S) : Borkur ARNVIDARSON et al.

It is certified that error appears in the above-indentified patent and that said Letters Patent is hereby corrected as shown below:

Column 16 Line 44, change "conversation" to --conversion--

Line 46, change "8" to --10--

Line 50, change "8" to --10--

Column 19 Line 17, change "30" to --32--

Signed and Sealed this

Fourth Day of August, 1998

Attest:

BRUCE LEHMAN

Attesting Officer

Commissioner of Patents and Trademarks